United States Patent
Frank

(10) Patent No.: US 6,926,007 B2
(45) Date of Patent: Aug. 9, 2005

(54) MEDICAL DEVICE FOR OVERCOMING AIRWAY OBSTRUCTION

(76) Inventor: Simon J Frank, 11400 SW. 94th Ave., Miami, FL (US) 33176

( * ) Notice: Subject to any disclaimer, the term of this patent is extended or adjusted under 35 U.S.C. 154(b) by 0 days.

(21) Appl. No.: 10/901,720

(22) Filed: Jul. 29, 2004

(65) Prior Publication Data

US 2005/0000521 A1 Jan. 6, 2005

Related U.S. Application Data

(63) Continuation of application No. 10/610,399, filed on Jun. 30, 2003.

(51) Int. Cl.[7] .............................. A61F 13/00; A61F 5/37
(52) U.S. Cl. ............. 128/846; 128/200.24; 128/202.18; 602/32
(58) Field of Search ................................ 601/41–44, 39, 601/24, 25; 128/845, 846, 876, 200.24, 202.18; 602/32–39

(56) References Cited

U.S. PATENT DOCUMENTS

| 3,461,858 | A | * | 8/1969 | Michelson | 601/41 |
| 3,469,268 | A | * | 9/1969 | Phillips | 602/19 |
| 3,509,899 | A | * | 5/1970 | Hewson | 137/87.04 |
| 4,297,999 | A | * | 11/1981 | Kitrell | 128/205.16 |
| 4,571,757 | A | * | 2/1986 | Zolecki | 5/628 |
| 5,494,048 | A | | 2/1996 | Carden | |
| 5,542,128 | A | * | 8/1996 | Lomas | 2/173 |
| 6,196,224 | B1 | | 3/2001 | Alfery | |
| 6,200,285 | B1 | | 3/2001 | Towliat | |
| 6,510,852 | B1 | * | 1/2003 | Shiery et al. | 128/845 |
| 2004/0016057 | A1 | * | 1/2004 | Traut et al. | 5/628 |

* cited by examiner

Primary Examiner—Henry Bennett
Assistant Examiner—Shumaya B. Ali
(74) Attorney, Agent, or Firm—Rhen Alcoba, Esq.; Laurence J. Edson, Esq.

(57) ABSTRACT

A medical device for overcoming airway obstruction featuring a flat rectangular support base with a support frame attached by a pivoting means. A T-band, so named for its shape and the positioning of its three straps, attaches to the support frame when the T-band is placed around the chin of a patient when the support base and support frame are perpendicular. Additionally, an adhesive layer is placed at the junction of the straps of the T-band, the layer configured for contact with a patient's chin.

7 Claims, 7 Drawing Sheets

MEDICAL DEVICE FOR OVERCOMING AIRWAY OBSTRUCTION

CROSS REFERENCE

The present application is a continuation i part of the inventor's U.S. patent Ser. No. 10/610,399 filed Jun. 30, 2003, entitled "Medical Device for Overcoming Airway Obstruction," currently pending, by inventor Simon Jacob Frank.

BACKGROUND

Obstruction of the upper airway by the tongue is a common complication when a sedated or unconscious patient is lying in the supine position. The causes of unconsciousness may be sedation, anesthesia, head trauma, drug overdose or any of a multitude of medical causes. The patient may be in any emergency situation. The direct cause it that gravity pulls the person's tongue downwards (towards the cervical spine) and the tongue obstructs the airway and impedes respiration, partially or completely. The airway obstruction discussed above might cause a life-threatening situation if the airway obstruction is not urgently cleared, for hypoxemia and death can quickly ensue.

Anesthesiologists commonly overcome airway obstruction by tilting the patient's head backwards and pulling the chin up towards the ceiling and away from the body (cephalad). Obstruction of the airway is overcome because the base of the tongue is attached to the mandible, and by pulling the chin upward the tongue will be simultaneously pulled upward. This practice is very fatiguing and restricts the anesthesiologist's or emergency responder's ability to perform other functions that require two free hands.

An upper airway can also be maintained open by inserting various medical tubes into the airway, for example, nasal-pharyngeal, oral-pharyngeal, laryngeal mask airway (LMA) and the cuffed oral pharyngeal. But as of today, there are no medical devices in common use that attach externally to the face that will maintain an open upper airway.

In the past, medical personnel have attempted to use surgical tape to attempt to maintain an open upper airway. Anesthesiologist would secure tape around the chin of a patient and then attach the ends of the tape to an operating room table. Tape procedures are unsatisfactory, for the tape attachment pulls back and downwards and do not provide the upward pull required on the chin to maintain an open upper airway. Tape quickly stretches and traction is lost. Tape is not sufficiently adherent to cope with the traction forces and detaches. Other complications with this procedure are skin trauma and eye damage. The tape passes close to the patient's eyes and contact with the eye is unavoidable if the patient coughs or turns the head. The method of attaching tape to the operating room table cannot be used to manage an obstructed airway outside of the operating room, example, at a roadside motor vehicle accident or during subsequent transportation to hospital.

Chin props comprising a ball on the end of an arm secured to the operating room table have also been used to push the chin up. They too have proven to be unsatisfactory and are not commonly used, because they are large and cumbersome and get in the way of surgeons operating on the upper body. Furthermore, if misapplied they may constrict the airway. Chin props with complex mechanisms that attach to suitable operating tables, cannot be used to manage an obstructed airway outside of the operating room, for example, at a roadside motor vehicle accident or during subsequent transportation to hospital.

Information relevant to attempts to address these problems can be found in U.S. Pat. Nos. 5,494,048, 6,200,285 B1, and 6,196,224 B1. However, each one of these references suffers from one or more of the following disadvantages:

1. Can cause eye damage and skin trauma;
2. Require attachment to suitable operating tables;
3. Obstruct the attendant's view of the patient;
4. Do not provide sufficient upward leverage to the chin;
5. Do not lend themselves to use in accident situations;
6. Do not effectively overcome airway obstruction; and
7. Difficulties in removal of devices, should immediate endotracheal intubation be required.

Inside and outside the operating room, an urgent need exists for equipment that overcomes upper airway obstruction and maintains an open upper airway. This equipment should be compatible with and improve the effectiveness of oral-pharyngeal and nasal-pharyngeal airways and face masks. In the operating room, such equipment would allow mask anesthesia to be used for sedated and anesthetized patients instead of general anesthesia and endotracheal intubation with immediate cost savings. Outside the operating room, a need exists for portable, compact equipment that can overcome upper airway obstruction and maintain an open airway and that can be used in cramped quarters such as an ambulance, a hyperbaric chamber and an MRI chamber.

For the foregoing reasons, there is a need for a medical device is safe and reliable that will overcome upper airway obstruction and that will maintain an open airway in the anesthetized and sedated patient lying in a supine position in an operating room and any unconscious patient lying in the supine position at any site. To be effective, the equipment should be safe and easy to use and reliable. The equipment should free up the operators' hands; render oral and nasal pharyngeal airways more effective and not interfere with but facilitate the use of a face mask. The equipment should be free standing, compact and portable.

SUMMARY

The present invention is directed to a medical device that assists in overcoming airway obstruction and maintaining an open airway when a patient, who may or may not be anesthetized, is unconscious and placed in the supine position, This device satisfies the following needs:

1. It frees the practitioner's hands to do other tasks;
2. Does not obstruct the view and allows the practitioner to visually monitor the patient;
3. It is compact and portable device;
4. It does not cause eye damage or skin trauma;
5. Does not require the use of specific operating room tables when operating the device; and
6. Allows for the easy removal of the device should the patient vomit or emergency endotracheal intubation be required.

The medical device for overcoming airway obstruction comprises of a rectangular cradle that has first and second portions, wherein the first portion has a length that is at least a distance that allows a patient's head to rest on and act as an anchor to the cradle and the second portion has a length that is at least a distance that allows a band to be placed under a patient's chin and encircle the second portion so that an upward pull can be generated on the chin by the band when the second portion is placed in a perpendicular position to the first portion, and the cradle's width is at least a distance that allows for the clearance of a patient's side facial features when the patient's head rests on the first portion of the cradle and a band is made to encircle the chin of a patient and attach to the second portion of the cradle; and a band that attaches to the second portion of the cradle when the second portion is perpendicular to the first portion.

One of the many advantages of this invention is the simplicity of its construction. The fact that the two main elements of this invention are a perpendicular portions and a band that can be easy attached to one of the portions of the plate after encircling the chin of a patient whose head rests on the other portion of the cradle after being placed in a supine position, attest to the simplicity of construction and use of this device. This invention takes precautions in preventing injuries that have been previously caused by the prior art, for example, eye damage or skin trauma. This invention also aids those in the emergency transportation field, for they need to have the maximum use of their hands when dealing with other aspects of emergency situations facing them. In addition, not having to worry whether the patient is breathing properly can allow emergency personnel to care for other injuries sustained by the patient and to attend to other patients.

A further advantage to this invention is that it is a stand-alone medical device. The device does not need to be attached to any supporting devices to become operable. When a patient's head is made to rest on one of the surfaces of the perpendicular portion, the weight of the patient's head on the portion is sufficient to secure the cradle so that an upward pull on the chin created between a band attached to the sides of the cradle not carrying the weight of the patient's head and the patient's chin will be maintained during the use of this device. Remember, as long as this upward pull is maintained, the upper airway will be maintained open, thus it is key that the tension created with this device not be compromised and this is easily solved by using the weight of the patient's head as the anchor to the device.

Yet another advantage to this invention is the placement of the band on the second portion insures that the band does not come in contact with the patient's eyes, this is very important for one cannot prevent coughing and other involuntary movements of the head.

DRAWINGS

These and other features, aspects, and advantages of the present invention will become better understood with regard to the following description, appended claims, and drawings where:

DESCRIPTION

Figure 1:
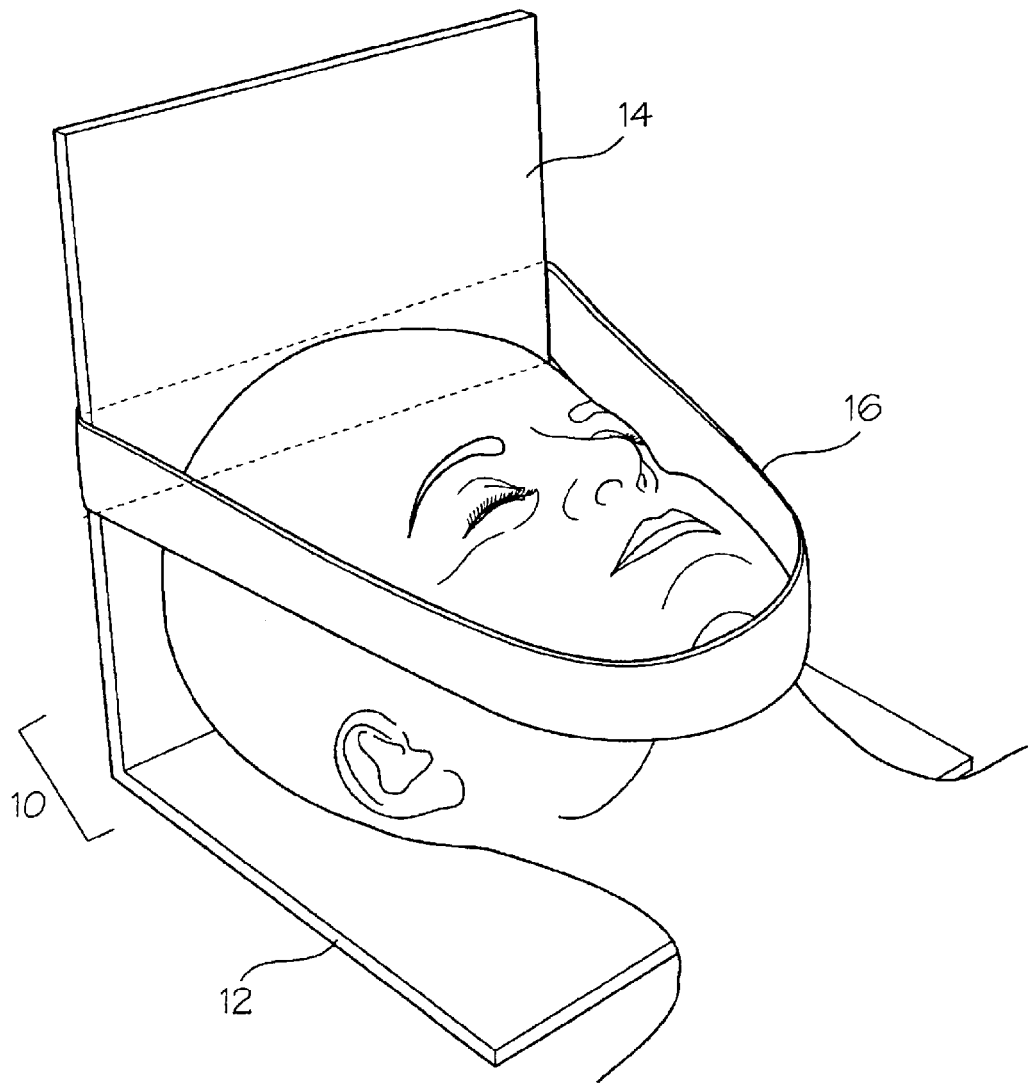
FIG. 1 shows a perspective view of the medical device in use with a patient in a supine position.

As shown in FIG. 1, a medical device used to overcome upper airway obstruction when a patient is in a supine position comprises a flat rectangular cradle 10 that has a first 12 and a second portion 14 wherein the first portion 12 has a length that is at least a distance that allows a patient's head to reset on and act as an anchor to the cradle and the second portion 14 is perpendicular to the first portion 12 and has a length that is at least a distance that allows a band 16 to be placed under a patient's chin and encircle the second portion 14 so that an upward pull can be generated on the chin by the band 16, and the cradle's width is at least a distance that allows for the clearance of a patient's side facial features when the patient's head rests on the first portion 12 of the cradle and a band 16 is made to encircle the chin of a patient and attach to the second portion 14 of the cradle; and a band 16 that attaches to the second portion 14 of the cradle when the second portion 14 is perpendicular to the first portion 12.

Figure 2:
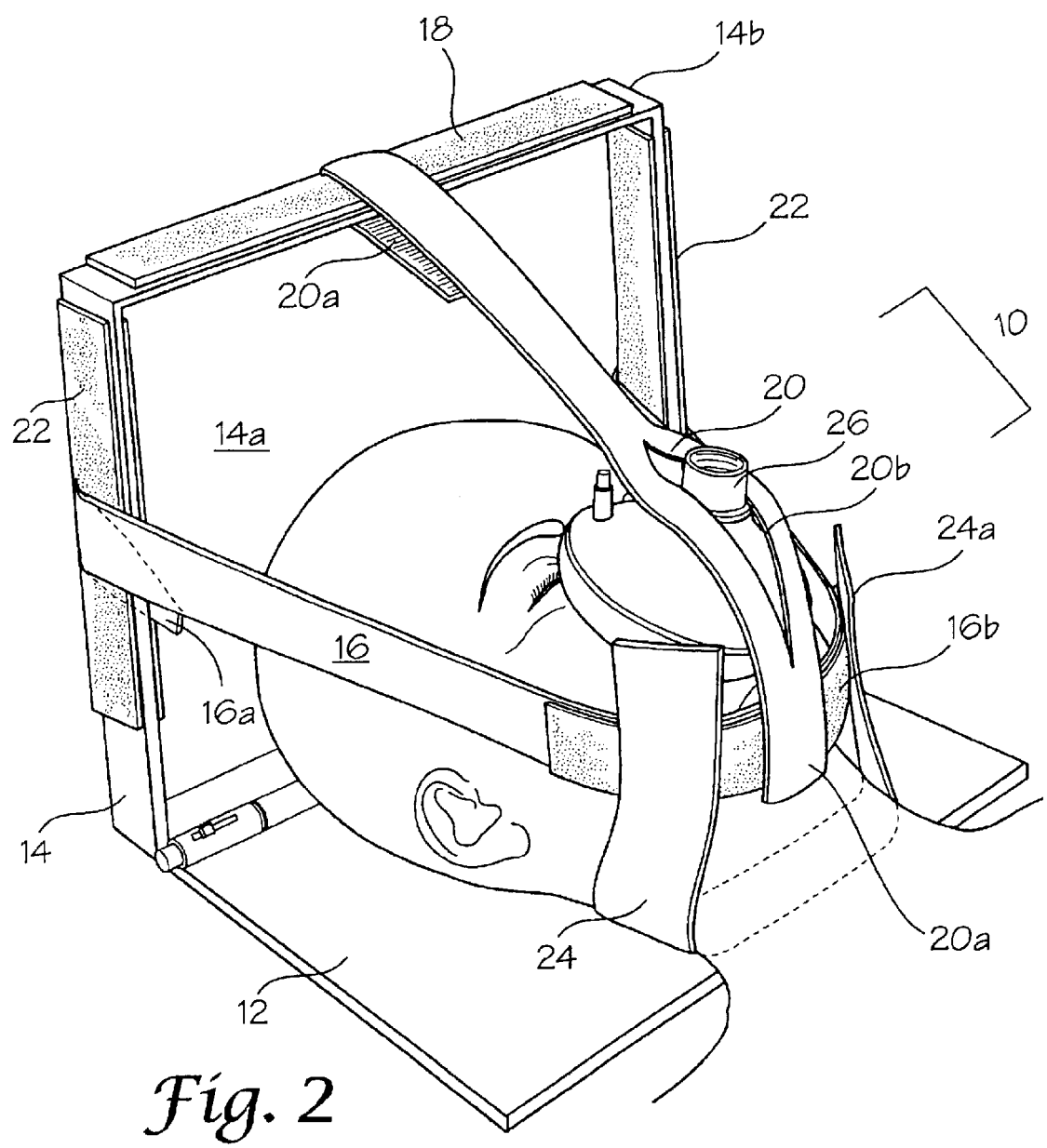
FIG. 2 shows a perspective view of another version of the medical device in use with a patient in a supine position.
Figure 3:
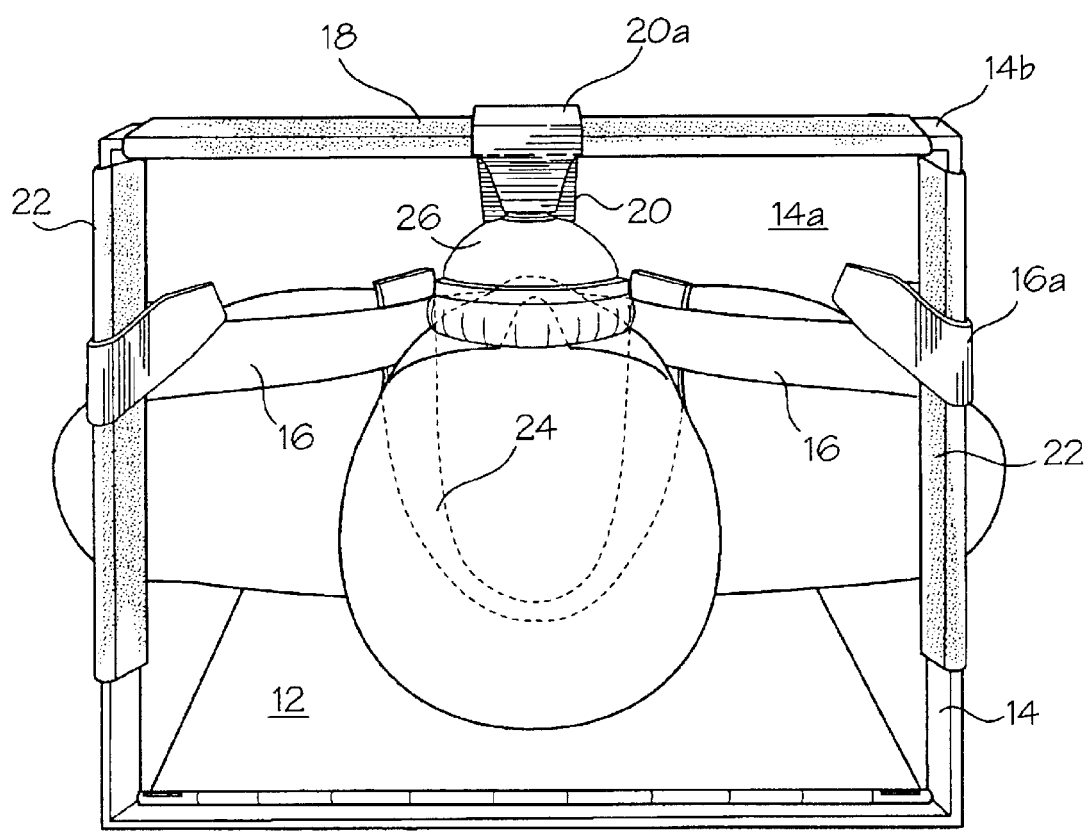
FIG. 3 shows a rear view of the medical device shown in FIG. 2, this view shows the second portion having an aperture within the second portion.

The cradle can be made of wood, stainless steel, plastics or polymers. The length of first 12 and second 14 portions of the cradle must be at least a 1 to 1 ratio. The length of the first portion 12 should be at least of a length that will allow a patients head to rest on it and act as an anchor to the medical device. The length of the second portion 14 should be of at least of a length that will create an upward pull on the chin of a patient when a band 16 is made to encircle the chin of the patient, when a patient is placed in a supine position, and the second portion 14 of the cradle 10. In a preferred embodiment of the invention, the length of the portions will be eight inches to twelve inches. Another embodiment of the invention has the first 12 and second 14 portions of the cradles being both eight inches in length. The width of the portions is to be at least eight inches, the preferred embodiment would have a width of twelve inches. The width has to be of sufficient length to allow for the clearance of the eyes when attaching the band 16 to the second portion 14 of the portion 10. As seen in FIG. 2 and FIG. 3, the second portion 14 of the cradle can define an aperture 14a that will merely make the second portion of the cradles a physical skeleton to attach the band 16 or straps yet to be defined.

The band can be made of an elastic material that has a degree of tension sufficient to pull the weight of a person's chin upward (when the patient is placed in a supine position) when encircling the second portion of the cradle and the chin of the patient. As seen in FIG. 2, the band 16 can also be made of fabric and have two ends, if the band 16 is made of fabric, then it is preferable that the ends of the bands 16a have either hook or pile fasteners. When using a fabric band 16, it is essential that the second portion 14 of the cradle have two receiving means 22 located on opposite sides on the second portion 14 and running along the length of the second portion 14 and situated a sufficient height to allow for an upward pull to be generated on the chin of a patient when the band 16 is placed around the chin of the patient and the ends of the band 16a are attached to receiving means 22 of the second portion 14 of the cradle. The receiving means 22 will also comprise of either hook or pile fasteners, depending on what type fasteners the ends of the band 16a utilize.

As seen in FIG. 2, the medical device can further comprise of having a middle attachment means 18 attached second portion 14 of the cradle (middle attachment means 18 can simply be glued on to the second portion 14), the middle attachment means 18 will attach to the second portion 14 at the outer extremity of the second portion 14a and be centered and run parallel along the width of the cradle 10. The attachment means 18 can be made of a fabric and contain hook or pile fasteners. The middle attachment means 18 is attached to a first strap 20, the first strap 20 has either hook or pile fasteners at its ends 20a (whether hook or pile fastener will depend on what type of attachment means the ends are connecting too). The first strap 20 will connect to the section (middle juncture) of the band 16b surrounding the chin of the patient using means known in the art (either hook or pile fasteners, this all depends on what type of fasteners the band has at the middle juncture of the band 16b to accommodate the connection). The first strap might define a first strap slit 20b running parallel along the length of the first strap. The first strap serves a duel purpose, the first purpose is to further apply upward pressure to the chin and the second purpose is to allow for the placement of a mask 26 within the slit the would cover the mouth and nose of the patient. The mask 26 would be used to provide either oxygen and/or an anesthetic to the patient.

The medical device can further comprise a second strap 24, the second strap 24 having attachment means located at the ends of the strap 24a (the attachment means would be either hook or pile fasteners). The second strap would encircle the rear of the patient's neck and would attach to the middle juncture of the band 16b fasteners. The only purpose for the second strap 24 is to secure the band 16 to the patient's chin, the invention does not require the second strap 24, it is used only as a safety precaution.

Figure 4A:
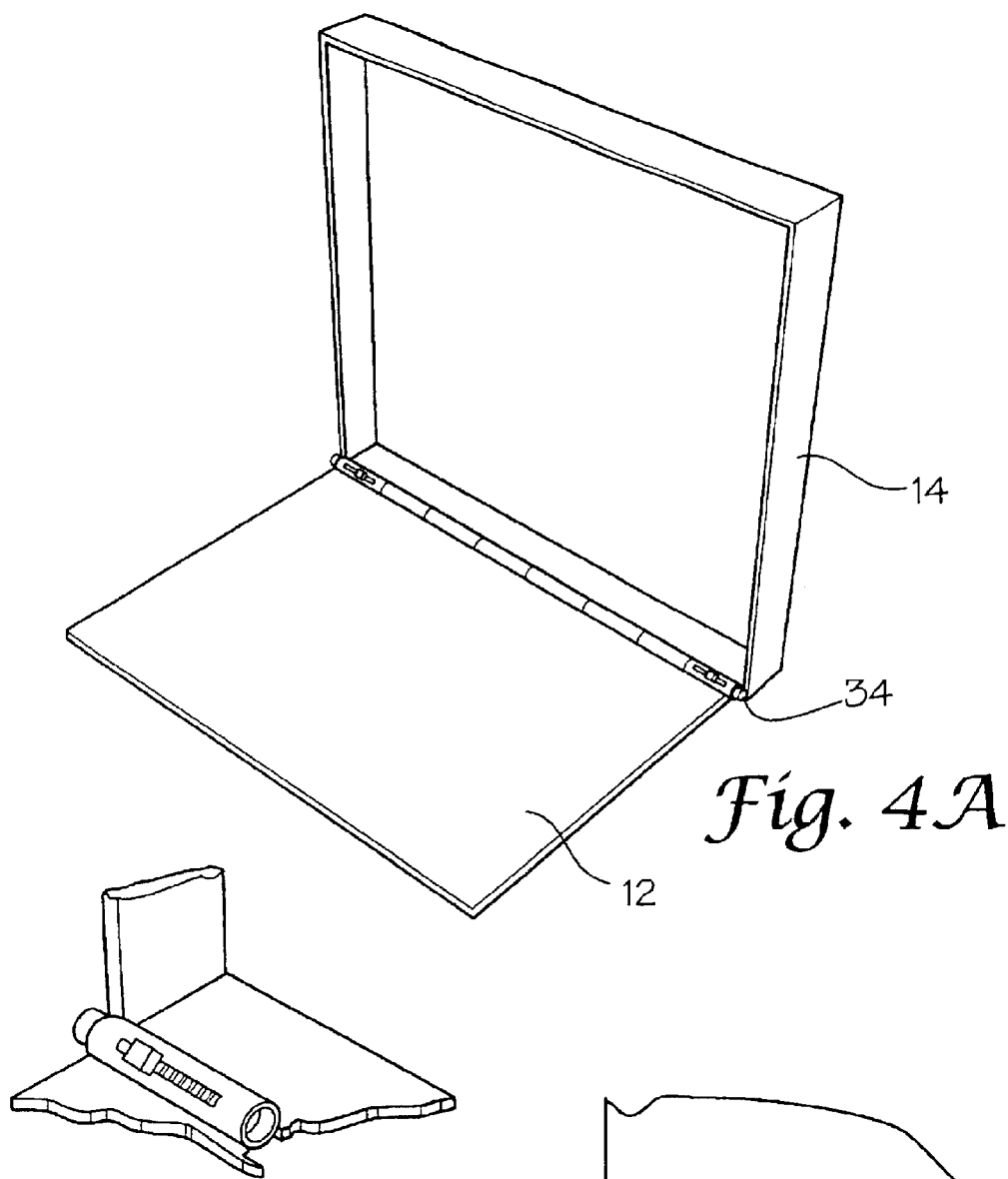
FIG. 4 shows a perspective view of another version of the present invention, this embodiment has a means for pivoting the portions and a locking means for maintaining the portions in a perpendicular position.
Figure 4B:
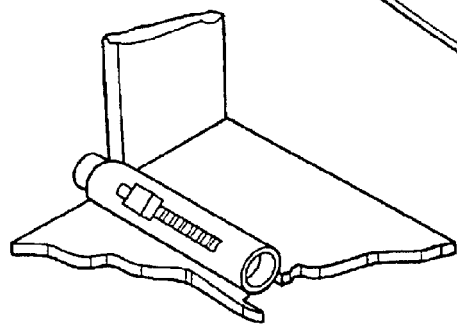
Figure 4C:
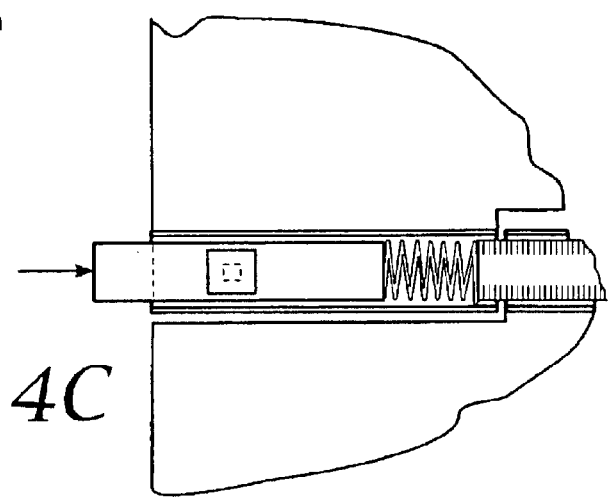
Figure 5:
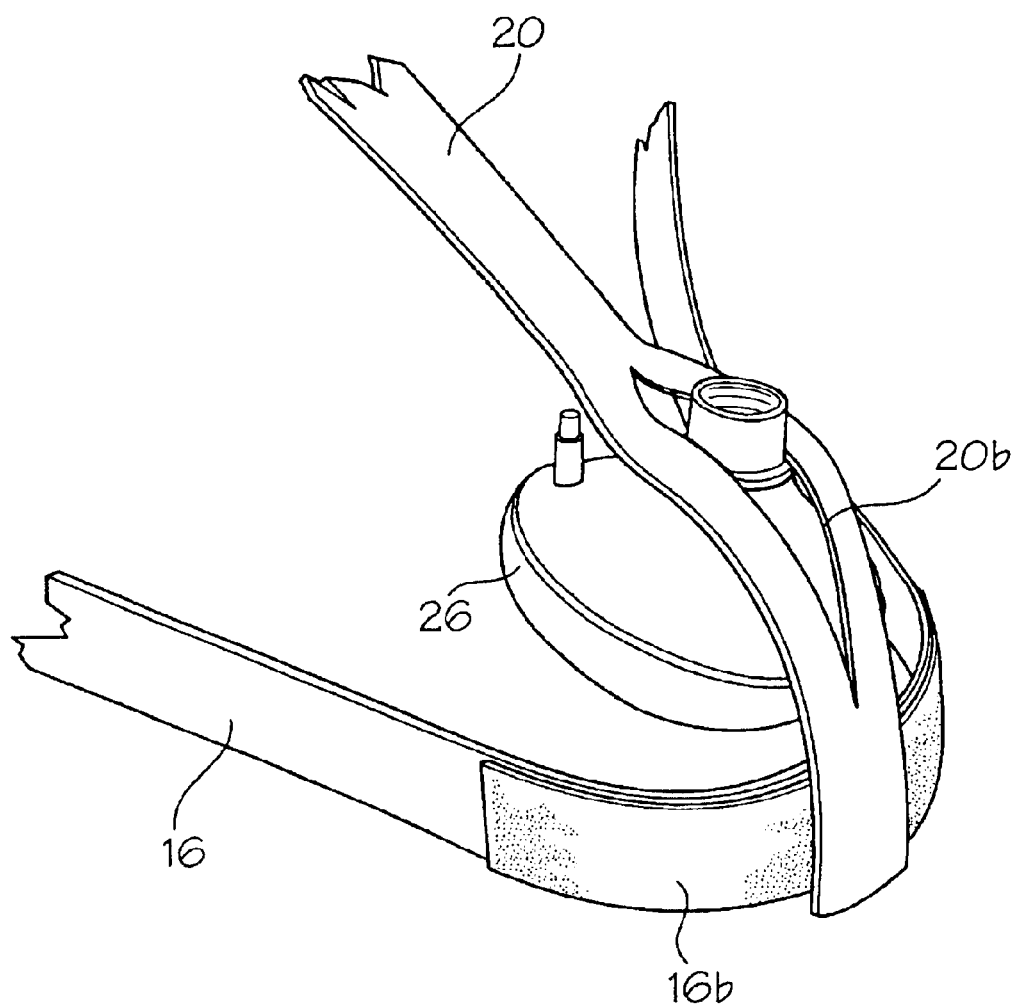
FIG. 5 shows a perspective of how the mask would attach to the first strap of the medical device and surround the nose and mouth of a patient in a supine position.

As seen in FIG. 4, another embodiment of the invention would comprise of a pivoting means 34 for folding the medical device. The pivoting means 34 would facilitate the transport of the device and would most likely be used in the field by emergency personnel, such as paramedics. The pivoting means 34 would connect the first 12 and second 14 portions of the cradles and have a closed locking position and an opening perpendicular locking position 36. The locking means would be incorporated into the pivot by means known in the art. As a safety precaution, the pivoting means, when placed in the perpendicular position would be placed so that they would not be able to rotate further than the perpendicular. This could simply be accomplished by inserting a screw along side the pivot(s) in either of the portions (allowing the head of the screw to be raised at least a few centimeters above the pivot) so that the portion not containing the screw could not be pivoted beyond the perpendicular. All of the previous elements discussed could be incorporated into this embodiment of the invention.

Figure 6:
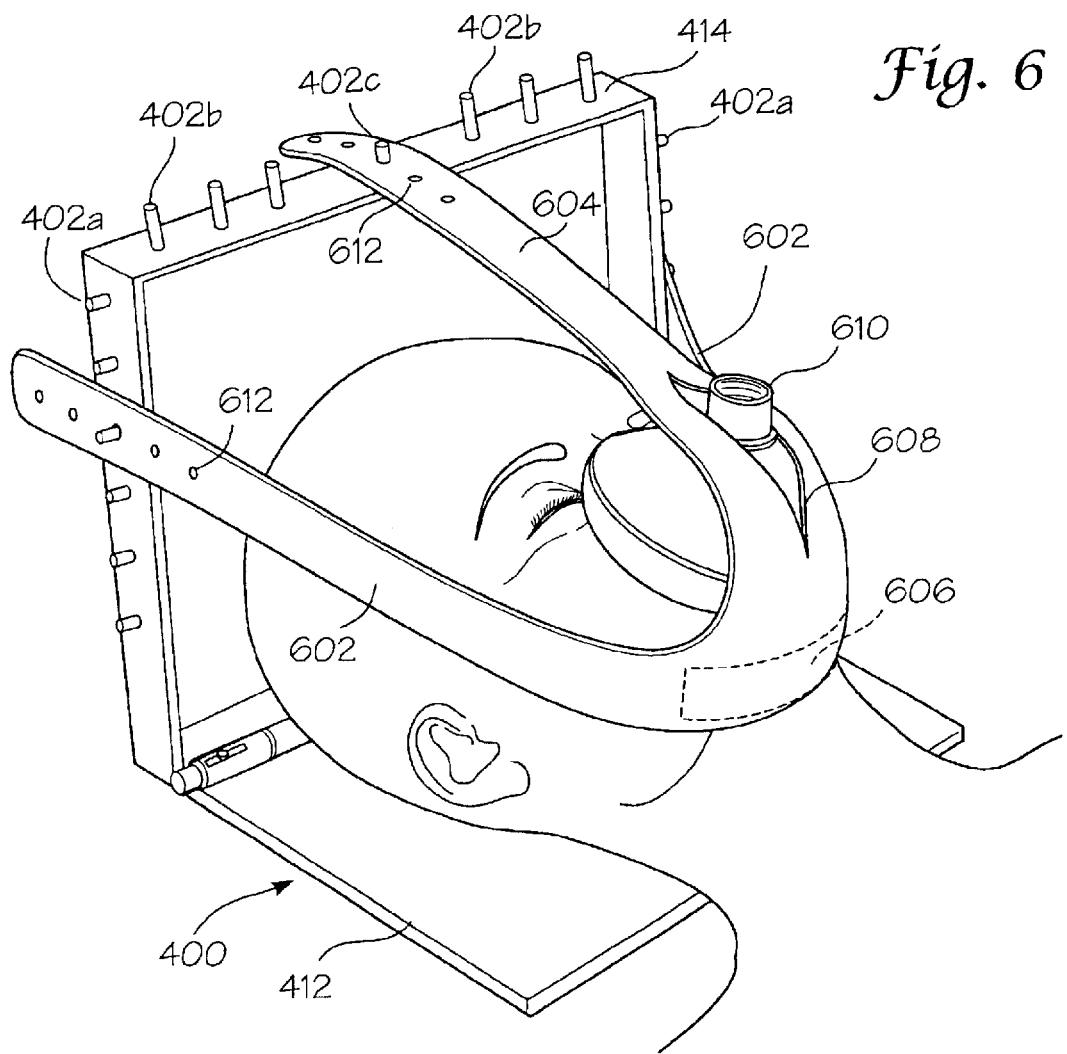
FIG. 6 shows a perspective view of another embodiment of the medical device in use with a patient in a supine position.

As shown in FIG. 6, in another embodiment of the medical device 400 used to overcome upper airway obstruction when a patient is in a supine position comprises a rectangular support base 412 that is attached to a support frame 414 by the pivoting means described above; and a T-band 600, as illustrated in FIG. 7, that attaches to the support frame 414 when the T-band 600 is placed around the chin of a patient when the medical device 400 is used.

The support frame 414 having a middle rod 402c that is located in the middle of the superior edge of the support frame 414 and six superior rods 402b located on the superior edge of the support frame 414, the superior rods 402b are positioned so that they are equally spaced from the middle rod 402c and run toward the outer edges of the support frame 414 in increments of one inch starting from the middle rod 402c outward, more specifically, three superior rods 402b are placed on each side of the middle rod 402c. The middle rod 402c measuring at least ⅛ of an inch in diameter and ¼ of an inch in height. Each superior rod 402b measuring at least ⅛ of an inch in diameter and ¾ of an inch in height. The support frame 414 further having 10 lateral rods 402a positioned on the lateral edges of the support frame 414, wherein the first of the lateral rods 402a is placed two inches from the superior edge of the support frame 414 and the remaining lateral rods 402a are positioned a distance of one inch from each other, more specifically, five lateral rods 402a are placed on each of the vertical sides of the support frame 414. Each lateral rod 402a measuring at least ⅛ of an inch in diameter and ¼ of an inch in height. In this embodiment of the invention, the superior edge of the support frame 414 shall have a length of 8 inches and the lateral edges of the support frame 414 having a length of twelve inches.

Figure 7:
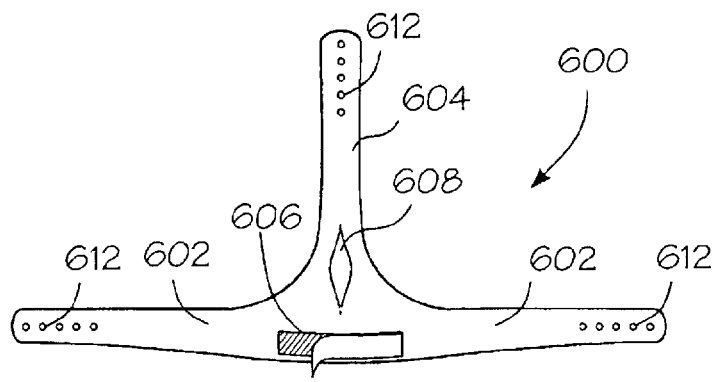
FIG. 7 shows a bottom view of the t-band piece of the medical device.
Figure 8:
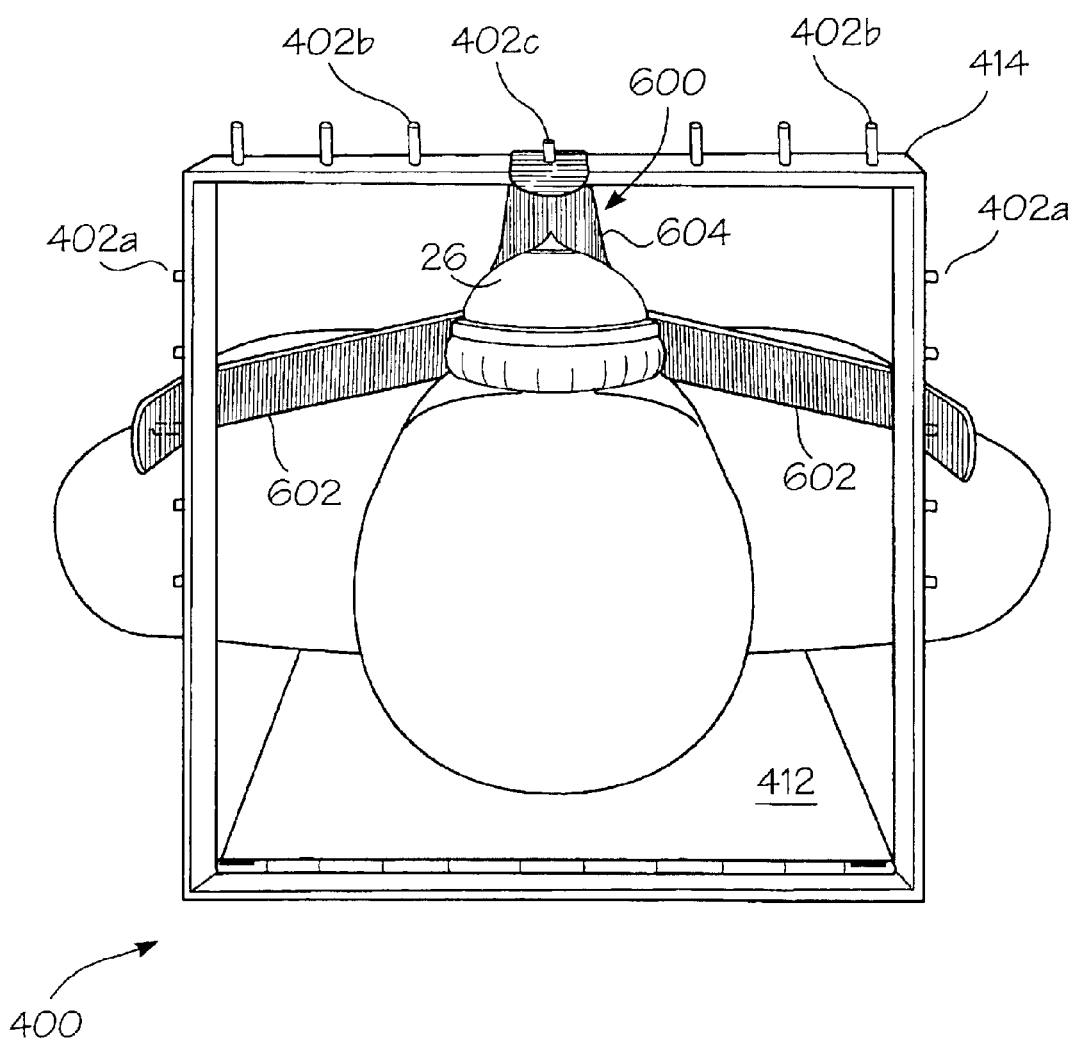
FIG. 8 shows a rear view of the medical device shown in FIG. 7.

As shown in FIG. 7, the T-band 600 is a three sided strap, wherein two sides 602 of the strap are perpendicular to a middle side 604 of the strap and each side strap 602 measures at least 12½ inches from where each side strap junctions with the middle strap 604. The middle strap shall measure at least 13½ inches from where the middle strap 604 junctions to the side straps 602. Each of the straps of the T-band 600 is at least 1¼ inches in width. The T-band 600 further defines a middle slit 608 that is defined within the middle strap 604 and runs from the junction of the straps toward the end of the middle strap 604, the middle slit 608 being at least 5½ inches in length. All of the straps shall define at least six fenestrations 612 starting one inch from the end of each strap and each fenestration 612 being ½ an inch apart from each other, each fenestration shall be at least 3/16 of an inch in diameter. The T-band 600 might further comprise an adhesive layer 606 that is placed at the junction of the T-band 600 so that the band bonds with the chin of patient when using the medical device 400.

A method of overcoming upper airway obstruction when a patient is in a supine position comprises the steps of placing the above mentioned medical device 10 on a flat surface, resting the back of a patient's head on the first portion 12 of the cradle, and encircling the chin of the patient with the band 16 and attaching the rest of the band to the second portion 14 of the cradle, the band's attachment to the second portion 14 would be in a position sufficiently high so that an upper pull can be generated on the chin of the patient.

The above method describes the most rudimentary use of the medical device described in this application. The medical device's main purpose is to prevent the blockage of the upper airway. As stated before, this is accomplished by pulling the chin up and away from the body. The band 16 pulls the chin upward and the second portion 14 of the cradle is used to ensure that the pressure applied to the chin is maintained while freeing the hands of the practitioner. The medical device can also be used as means to secure a mask 26 to the face of a patient.

An advantage of the present invention is that a patient's eyes are never in danger of being damaged, for when the band is placed to encircle the chin of the patient and then attached to the second portion of the cradle, the band attaches to the second portion of the cradle at a position that does not allow the band to rub against the eyes.

Another advantage of the present invention is that when using the embodiment that defines an aperture in the second portion of the cradle, a patient can be monitored from behind the patient, there is no obstruction to seeing the patient.

A further advantage of the present invention is that it is compact and rudimentary in its nature. The device can be made operational by simply placing the device on a flat surface, placing a patient's head on the device (the patient being in a supine position) and encircling an elastic band around the patient's chin and the second portion of the cradle.

Yet a further advantage to the device is that it does not require attachment to other structures to become operational, it is the ideal device for practitioners working in the field, paramedics.

Another advantage of the invention is the simplicity in which it can be taken off a patient should an emergency situation arise, one would simply pull the bands off the hook and pile fasteners.

Finally, another advantage of this device is that it frees the hands of the operator, thereby allowing the attendant to treat other problems that the patient might be experiencing and to attend to other patients.

Although the present invention has been described in considerable detail with reference to certain preferred versions thereof, other versions are possible. Therefore the spirit and the scope of the claims should not be limited to the description of the preferred versions contained herein.

What is claimed is:

1. A medical device used to overcome upper airway obstruction when a patient is placed in a supine position comprising:
    a flat rectangular support base;
    a support frame having superior, and lateral sides;
    a pivoting means attaching the flat rectangular support base to the support frame; and
    a T-band attaching the support frame when the T-band is placed around the chin of a patient when the support base and frame are perpendicular.

2. The medical device of claim 1, wherein the superior edge of the support frame measures 8 inches in length and the lateral edges of the support frame measure twelve inches in length, and wherein the support frame further comprises:
    a middle rod positioned in the middle of the superior edge of the support frame;
    six superior rods located on the superior edge of the support frame, the superior rods positioned so that they are equally spaced from the middle rod and run toward the outer edges of the support frame in increments of one inch starting from the middle rod outward, whereby, three superior rods are on each side of the middle rod; and
    ten lateral rods positioned on the lateral edges of the support frame, wherein the first of the lateral rods is placed two inches from the superior edge of the support frame and the remaining lateral rods are positioned a distance of one inch from each other, more specifically, five lateral rods are placed on each of the vertical sides of the support frame.

3. The medical device of claim 2, wherein the T-band is a three sided strap, and two sides of the strap are perpendicular to a middle side of the strap and each side strap measures at least 12½ inches from where each side strap junctions with the middle strap, the middle strap measures at least 13½ inches from where the middle strap junctions with the side straps.

4. The medical device of claim 3, wherein each strap of the T-band is at least 1¼ inches in width.

5. The medical device of claim 4, wherein the T-band further defines a middle slit that is defined within the middle strap and runs from the junction of the straps toward the end of the middle strap, the middle slit being at least 5½ inches in length.

6. The medical device of claim 5, wherein all of the straps of the T-band define at least six fenestrations starting one inch from the end of each strap.

7. The medical device of claim 6, wherein the T-band further comprises an adhesive layer placed at the junction of the T-band so that the band bonds to the chin of patient when using the medical device.

* * * * *